United States Patent
Roso et al.

(10) Patent No.: US 7,902,135 B2
(45) Date of Patent: *Mar. 8, 2011

(54) METHOD OF IMPROVING THE OCULAR TOLERANCE OF FOAMING AND/OR DETERGENT COMPOSITIONS FOR SKIN USE

(75) Inventors: Alicia Roso, Saix (FR); Chantal Amalric, Blan (FR); Guy Tabacchi, Paris (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 170 days.

This patent is subject to a terminal disclaimer.

(21) Appl. No.: 12/294,364

(22) PCT Filed: Mar. 16, 2007

(86) PCT No.: PCT/FR2007/050941
§ 371 (c)(1),
(2), (4) Date: Sep. 24, 2008

(87) PCT Pub. No.: WO2007/110526
PCT Pub. Date: Oct. 4, 2007

(65) Prior Publication Data
US 2009/0258808 A1    Oct. 15, 2009

(30) Foreign Application Priority Data
Mar. 24, 2006   (FR) ..................... 06 51019

(51) Int. Cl.
*A61K 8/60* (2006.01)
*A61K 8/73* (2006.01)
*A61Q 19/10* (2006.01)

(52) U.S. Cl. ....... 510/130; 510/129; 510/136; 424/70.13
(58) Field of Classification Search ................. 510/130, 510/129, 136; 424/70.13
See application file for complete search history.

(56) References Cited

U.S. PATENT DOCUMENTS

| 2002/0123438 A1 | 9/2002 | Pflederer et al. | |
| 2004/0241127 A1* | 12/2004 | Roso et al. | 424/70.13 |
| 2005/0069512 A1* | 3/2005 | Roso et al. | 424/70.13 |
| 2006/0088491 A1* | 4/2006 | Stoltz et al. | 424/70.13 |
| 2009/0088358 A1* | 4/2009 | Roso et al. | 510/130 |

FOREIGN PATENT DOCUMENTS

| DE | 100 44 662 | 3/2002 |
| WO | WO 86/01512 | 3/1986 |
| WO | WO 03/094864 | 11/2003 |

OTHER PUBLICATIONS

International Search Report dated Sep. 21, 2007, in PCT application.

* cited by examiner

*Primary Examiner* — Douglas McGinty
(74) *Attorney, Agent, or Firm* — Young & Thompson

(57) ABSTRACT

The ocular tolerance of cosmetic, dermocosmetic and dermopharmaceutical compositions is improved by the incorporation therein of an effective amount of a polyol-glycoside or of a mixture of polyol-glycosides of formula (I): $R_1$—O-(G)-H (I) in which: —x represents a decimal number between 1 and 5 and G represents the residue of a reducing sugar, and $R_1$ represents a radical of formula (A) —$CH_2$—$(CHOH)_n$—$CH_2$—OH (A) in which n is an integer equal to 2, 3 or 4, or else $R_1$ represents a radical of formula (B) —$(CH_2$—CHOH—$CH_2$—O$)_m$—H (B) in which m is an integer equal to 1, 2 or 3. The invention also relates to new concentrates which contain compounds of formula (I), foaming and/or detergent surfactants and topically acceptable solvents, and also to processes for preparing them.

7 Claims, No Drawings

METHOD OF IMPROVING THE OCULAR TOLERANCE OF FOAMING AND/OR DETERGENT COMPOSITIONS FOR SKIN USE

A subject matter of the present invention is a novel method for improving the ocular tolerance of compositions for topical use, in particular foaming and/or detergent compositions, novel concentrates having improved ocular tolerance and their process of preparation.

The invention finds use preferably in the cosmetic and dermocosmetic field and in the dermopharmaceutical and pharmaceutical field, but also in the field of the textile industry, for example for the treatment of synthetic or natural and woven or knitted textile fibers, or also in the field of the papermaking industry, for example in the manufacture of paper for sanitary or domestic use.

The development of cleaning formulations for the face and for the hair, presented in the form of shampoos or lotions, requires formulations that have good ocular tolerance. This concern is particularly important in the development of cleaning formulations for babies and children but it also constitutes a requirement for the adult users of these products. Moreover, the search for good ocular tolerance is also extended to all washing products for the body, shower gels and foam baths.

Moreover, the generation of foam by these formulations when they are used constitutes a key element in the performances required as the consumer regards it as a critical indicator of the effectiveness of the cleaning.

Several categories of surfactants are used in the preparation of formulations having a cleaning purpose: cationic, anionic, amphoteric or nonionic surfactants.

Anionic surfactants, such as sulfate-comprising anionic surfactants, constitute a class of surfactants frequently used due to their good foaming properties. However, these surfactants cause intolerance and/or irritation reactions, in particular with regard to the eyes and/or skin.

In order to reduce the scale of these phenomena, without however eliminating them completely, it is preferable rather to use alkyl ether sulfates than alkyl sulfates. Another solution, itself also partially satisfactory, consists in combining these sulfate-comprising surfactants with amphoteric surfactants, such as betaines, for example Amonyl™ 380BA and Amonyl™ 675SB, sold by Seppic, with cationic surfactants, such as "cocoamidopropyl betainamide MEA chloride", sold under the name "Montaline™ C40 by Seppic, or cetyltrimonium ammonium chloride, sold under the name Dehyquart™ ACA from Cognis, or also with acylates of proteins or acylated derivatives of amino acids, such as triethanolamine cocoyl glutamate, sold under the name Acylglutamate™ C12S by Ajinomoto. The majority of these combinations prove, however, to be relatively ineffective in reducing ocular irritation and this problem remains even if the anionic surfactants are completely eliminated in order to replace them with these amphoteric or cationic surfactants.

Another solution for improving the ocular tolerance of cleaning formulations consists in combining the sulfate-comprising surfactants with surfactants of ethoxylated nonionic type. Examples which have been tried out are combinations with ethoxylated sorbitan esters, such as Polysorbate 20 or Polysorbate 60, sold by Seppic under the respective names Montanox™ 20 and Montanox™ 60, and such as PEG-80 sorbitan laurate, sold under the name Montanox™ MLS 80 by Seppic, or combinations with ethoxylated glycerol esters, such as that combining PEG-40 glyceryl cocoate and sodium coceth sulfate in the composition sold by Seppic under the name Oronal™ LCG. Such compositions, while they make it possible to effectively reduce ocular irritation when the amount of ethoxylated nonionic cosurfactants is used in high proportions and represents at least 40% of the dry matter of the alkyl ether sulfate/ethoxylated nonionic cosurfactant mixture, however have the consequence of very significantly reducing the volume of foam formed during use by the consumer and, in some cases, of detrimentally affecting the stability of the foam over time.

The international application published under the number WO 03/094864 describes a shower gel comprising sodium lauryl ether sulfate and a mixture of xylitol and xylityl glucoside.

The United States of America patent application published under the number US 2002/0123438 A1 discloses a detergent composition which is not very irritating to the eyes comprising an acrylic copolymer with a hydrophobic chain, a polyol polyalkoxy ester and an anionic surfactant.

The inventors have thus sought to develop a novel solution for improving the ocular tolerance of cosmetic, dermocosmetic, dermopharmaceutical or pharmaceutical compositions.

For this reason, according to a first aspect, a subject matter of the invention is a method for improving the ocular tolerance of a composition for topical use, characterized in that an effective amount of a compound of formula (I):

$$R_1-O-(G)_x-H \qquad (I)$$

in which:
x represents a decimal number of between 1 and 5,
G represents the residue of a reducing sugar, and
$R_1$ represents a monovalent radical of formula (A):

$$-CH_2-(CHOH)_n-CH_2-OH \qquad (A)$$

in which n is an integer equal to 2, 3 or 4, or else
$R_1$ represents a monovalent radical of formula (B):

$$-(CH_2-CHOH-CH_2-O)_m-H \qquad (B)$$

in which m is an integer equal to 1, 2 or 3,
or of a mixture of compounds of formula (I), is incorporated in said composition.

The term "effective amount" denotes, in the definition of the method as defined above, an amount such that the final composition obtained by said method has an HET-CAM index of less than 5 and preferably of less than or equal to 3. The method for determining such an index is described in section B of the experimental part of the present account. According to a specific form of the method as defined above, the term "effective amount of compound of formula (I)" denotes a proportion by weight of 0.5% to 10% of the final composition and very particularly of 1% to 5%.

The expression "for topical use" used in the definition of the method as defined above means that said composition is employed by application to the skin, hair, scalp or mucous membranes, whether a direct application, in the case of a cosmetic, dermocosmetic, dermopharmaceutical or pharmaceutical composition, or an indirect application, for example in the case of a body hygiene product in the form of a textile or paper wipe or sanitary products intended to be in contact with the skin or mucous membranes.

The term "reducing sugar" denotes, in the definition of the formula (I) of the compound employed in the method as defined above, saccharide derivatives which do not exhibit, in their structures, a glycoside bond established between an anomeric carbon and the oxygen of an acetal group, such as are defined in the reference work: "Biochemistry", Daniel Voet/Judith G. Voet, p. 250, John Wiley & Sons, 1990). The oligomeric structure $(G)_x$ can be provided in any isomeric form, whether relating to optical isomerism, geometric isomerism or position isomerism; it can also represent a mixture of isomers. In the formula (I) as defined above, the R₁—O— group is bonded to G via the anomeric carbon of the saccharide residue, such as to form an acetal functional group.

According to another specific aspect of the method as defined above, in the formula (I), G represents the residue of a reducing sugar chosen from glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose.

According to another specific aspect of the method as defined above, in the formula (I), G represents the residue of a reducing sugar chosen from glucose, xylose or arabinose.

According to a specific aspect of the present invention, a subject matter of the invention is a method as defined above in which the composition for topical use comprises at least one foaming and/or detergent surfactant.

The term "foaming and/or detergent surfactant" denotes the topically acceptable anionic, cationic, amphoteric or nonionic surfactants commonly used in this field of activity.

Mention will particularly be made, among anionic surfactants which can be combined with these compounds and with these concentrates, of alkali metal salts, alkaline earth metal salts, ammonium salts, amine salts or aminoalcohol salts of the following compounds: alkyl ether sulfates, alkyl sulfates, alkylamido ether sulfates, alkylaryl polyether sulfates, monoglyceride sulfates, α-olefin sulfonates, paraffin sulfonates, alkyl phosphates, alkyl ether phosphates, alkylsulfonates, alkylamidesulfonates, alkylarylsulfonates, alkyl carboxylates, alkyl sulfosuccinates, alkyl ether sulfosuccinates, alkylamide sulfosuccinates, alkyl sulfoacetates, alkylsarcosinates, acylisethionates, N-acyltaurates, or acyllactylates. Mention will also be made, among anionic surfactants, of lipoamino acids, lipoproteins, lipopeptides, lipoprotein derivatives, protein derivatives, salts of fatty acids or salts of acids of optionally hydrogenated coconut oil.

Mention will particularly be made, among amphoteric surfactants which can be combined with these compounds and with these concentrates, of alkyl betaines, alkyl amido betaines, sultaines, alkyl amidoalkyl sulfobetaines, imidazoline derivatives, phospho-betaines, amphopolyacetates and amphopropionates.

Mention will particularly be made, among cationic surfactants which can be combined with these compounds and with these concentrates, of quaternary ammonium derivatives.

Mention will particularly be made, among nonionic surfactants which can be combined with these compounds and with these concentrates, of alkylpolyglycosides, castor oil derivatives, polysorbates, coconut amides, N-alkylamines or amine oxides. The abovementioned foaming and/or detergent surfactants which are anionic surfactants more particularly include the compounds of formula (II):

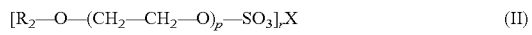

$$[R_2-O-(CH_2-CH_2-O)_p-SO_3]_rX \quad (II)$$

in which:
R₂ represents a saturated or unsaturated and linear or branched aliphatic hydrocarbon radical comprising from 6 to 22 carbon atoms,
p represents a decimal number of between 1 and 10, preferably between 2 and 4,
r is an integer equal to 1 or to 2, and
X represents the cation of an alkali metal or of an alkaline earth metal, the ammonium ion, the (hydroxyethyl)ammonium ion, the tri(hydroxy-ethyl)ammonium ion or a mixture of compounds of formula (II).

In the formula (II) as defined above, X represents, for example, sodium or magnesium or the ammonium ion.

According to another specific aspect of the method as defined above, the ratio by weight of compounds of formula (I) to foaming and/or detergent surfactants present in said composition for topical use is between 1/10 and 10/1, more particularly between 1/10 and 1/1.

According to a second aspect, a subject matter of the invention is a concentrate comprising, per 100% of its weight:
from 8% to 90% by weight of a compound of formula (I):

$$R_1-O-(G)_x-H \quad (I)$$

in which:
x represents a decimal number of between 1 and 5,
G represents the residue of a reducing sugar, and
R₁ represents a monovalent radical of formula (A):

$$-CH_2-(CHOH)_n-CH_2-OH \quad (A)$$

in which n is an integer equal to 2, 3 or 4, or else
R₁ represents a monovalent radical of formula (B):

$$(CH_2-CHOH-CH_2-O)_m-H \quad (B)$$

in which m is an integer equal to 1, 2 or 3,
or of a mixture of compounds of formula (I);
from 2% to 99% by weight of a compound of formula (II):

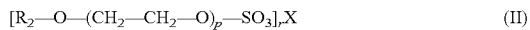

$$[R_2-O-(CH_2-CH_2-O)_p-SO_3]_rX \quad (II)$$

in which:
R₂ represents a saturated or unsaturated and linear or branched aliphatic hydrocarbon radical comprising from 6 to 22 carbon atoms,
p represents a decimal number of between 1 and 10, preferably between 2 and 4,
r is an integer equal to 1 or to 2, and
X represents the cation of an alkali metal or an alkaline earth metal, the ammonium ion, the (hydroxyethyl)ammonium ion or the tri(hydroxy-ethyl)ammonium ion,
or of a mixture of compounds of formula (II); and
from 0% to 80% by weight of a topically acceptable solvent.

The term "topically acceptable solvent" denotes, in the context of the present invention, the solvents known to a person skilled in the art which can be applied to human and/or animal skin, to the scalp and to mucous membranes. The topically acceptable solvent is chosen in particular from one or more components of a group consisting of water, glycols, polyols, alcohols, alkoxylated polyols and glycol ethers, and more particularly from one or more components of a group consisting of water, ethanol, isopropanol, butylene glycol, hexylene glycol, caprylyl glycol or 1,2-octanediol, pentylene glycol or 1,2-pentanediol, ethylhexylglycerin or octoxyglycerin, glycerol, diglycerol, triglycerol, erythritol, xylitol, sorbitol, butyl diglycol, polyethylene glycols, the molecular weight of which is between 200 g/mol and 8000 g/mol, monopropylene glycol, dipropylene glycol and 2-methyl-1,3-propanediol.

Advantageously, the abovementioned topically acceptable solvent is chosen from water and from one or more components of the group of the polyols consisting of xylitol, erythritol, sorbitol, glycerol and diglycerol.

The compounds of formula (I) or the mixtures of compounds of formula (I), the compounds of formula (II) and the topically acceptable solvent can be incorporated in the cosmetic composition for topical use separately or else in the form of a concentrate which is a subject matter of the invention. Furthermore, according to one or more routes for the preparation of the compounds of formula (I) or of the mixtures of compounds of formula (I), which consist in reacting a reducing sugar G with a polyol of formula (A1):

in which n is an integer equal to 2, 3 or 4, and/or of formula (B1):

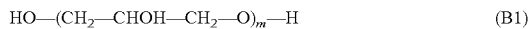

in which m is an integer equal to 1, 2 or 3,
the amount of unreacted polyol, when the latter has been selected from one or more components of the group defined above, can constitute all or part of the topically acceptable solvent. In this case, the compounds of formula (I) or the mixtures of compounds of formula (I) and the topically acceptable solvent are concomitantly incorporated in the cosmetic composition for topical use and the compounds of formula (II) can be incorporated in a subsequent stage.

According to a specific form of the concentrate as defined above, in the formula (I), G represents the residue of a reducing sugar chosen from glucose, xylose and arabinose.

According to another specific form of the concentrate as defined above, in the formula (II), $R_2$ represents a saturated aliphatic hydrocarbon radical comprising from 8 to 18 carbon atoms.

According to another specific form of the concentrate as defined above, it comprises, per 100% of its weight:
from 8% to 50% by weight of a compound of formula (I) or of a mixture of compounds of formula (I),
from 10% to 95% by weight of a compound of formula (II) or of a mixture of compounds of formula (II), and
from 0 to 80% by weight of a topically acceptable solvent.

The concentrate which is a subject matter of the invention can be obtained by various routes.

A first synthetic route consists, in a first stage (a), in introducing a compound of formula (I) or a mixture of compounds of formula (I) and a compound of formula (II) or a mixture of compounds of formula (II) into a reactor according to a controlled ratio by weight and in subjecting this mixture to efficient mechanical stirring under temperature conditions which make it possible to ensure the homogeneity of the mixture, preferably between 20° C. and 90° C.

If necessary, a second stage (b) consists in introducing a topically acceptable solvent as defined above into the mixture obtained during stage (a), and in continuing the stirring until a homogeneous concentrate is obtained.

A second route for the synthesis of the concentrate according to the invention consists in synthesizing, during a first stage (a1), the compound of formula (I) or the mixture of compounds of formula (I) by introducing a reducing sugar and a polyol of formula (A1) or (B1), such as, for example, erythritol, xylitol, glycerol, diglycerol, triglycerol or sorbitol, into a reactor according to a controlled stoichiometric ratio and in subjecting this mixture to an acetalization reaction under predetermined temperature and partial vacuum conditions in the presence of an acid catalytic system. The components of this acid catalytic system will generally be chosen from sulfuric, hydrochloric, phosphoric, nitric, hypophosphorous, methanesulfonic, para-toluenesulfonic or trifluoromethanesulfonic acids and acidic ion-exchange resins. Usually, the acetalization reaction will be carried out at a temperature of 70 to 130° C. under a vacuum of 300 to 20 mbar. During a second stage (b1), a compound of formula (II) or a mixture of compounds of formula (II) is mixed with the reaction product obtained during stage (a1) via a stirring system which makes it possible to achieve a homogeneous concentrate.

If necessary, a third stage (c1) consists in introducing a topically acceptable solvent as defined above into the mixture obtained during stage (b1) and in continuing the stirring until a homogeneous concentrate is obtained.

A third synthetic route consists in subjecting the polyol of formula (A1) or (B1) to dehydration in the presence of an acid catalytic system at a temperature of between 70° C. and 130° C. under partial vacuum with concomitant elimination of the water formed during the intramolecular rearrangement undergone by the polyol during a first stage (a2); and in then acetalizing the dehydrated polyol thus obtained by dispersion of a reducing sugar in the reaction medium and by maintaining the latter at a temperature of between 80° C. and 130° C. under partial vacuum during a second stage (b2).

The acid catalytic system used in this third synthetic route can be identical to that mentioned for the second route.

If necessary, a third stage (c2) consists in introducing a topically acceptable solvent as defined above into the mixture obtained during stage (b2) and in continuing the stirring until a homogeneous concentrate is obtained.

A fourth route for synthesis by transacetalization consists in: preparing butyl glucoside by reaction between butanol and glucose in the presence of an acid catalytic system at a temperature of between 90° C. and 105° C. under partial vacuum with concomitant elimination of the water formed during the reaction during a first stage (a3), it being possible for the acid catalytic system used to be identical to that mentioned for the preceding synthetic routes; adding a polyol of formula (A1) or (B1) to the reaction medium thus obtained with removal by distillation under vacuum of the residual butanol, of the butanol formed during the transacetalization reaction and of the water possibly generated during the intramolecular rearrangement of said polyol during a second stage (b3); and, if necessary, a third stage (c3) consists in introducing a topically acceptable solvent as defined above into the mixture obtained during stage (b3) and in continuing the stirring until a homogeneous concentrate is obtained.

According to a third aspect, a subject matter of the invention is the use of a compound of formula (I), of a mixture of compounds of formula (I) or of the concentrate as defined above, in improving the ocular tolerance of a cosmetic, dermocosmetic, dermopharmaceutical or pharmaceutical composition for topical use.

The compounds of formula (I), the mixtures of compounds of formula (I) and the concentrates as defined above can be incorporated in any type of cosmetic, dermocosmetic, dermopharmaceutical or pharmaceutical composition intended for topical use or else in any type of support intended to be brought into contact with the skin (paper, wipe, textile, transdermal device, and the like). The cosmetic compositions for topical use in which an effective amount of compounds of formula (I) or of mixtures of compounds of formula (I) is incorporated, and which optionally comprise one or more foaming and/or detergent surfactants, or else the concentrates defined above, can be applied without distinction to the skin, to the hair, to the scalp or to the mucous membranes and are provided in particular in the form of a solution, of an emulsion or of a microemulsion of the water-in-oil (W/O) or oil-in-water (O/W) type, of a multiple emulsion of water-in-oil-in-water (W/O/W) or oil-in-water-in-oil (O/W/O) type, of a gel, of a soap, of a balm, of a hydrodispersion, of a solid stick, of an ointment, of a cream, of a foam or of an aerosol, or also in the anhydrous form, such as a powder. These compositions can be used as cleansing or makeup-removing milks, as cleansing or makeup-removing lotions, as foaming gels for the face or for the body, as shampoos or conditioners, or as foam bath.

Generally, these compositions comprise, in addition to the foaming and/or detergent surfactants which may optionally be present therein, excipients and/or active principles normally employed in the field of formulations for topical use, in particular cosmetic, dermocosmetic, pharmaceutical or dermopharmaceutical formulations, thickeners, gelling agents, stabilizing agents, film-forming compounds, solvents and cosolvents, hydrotropic agents, plasticizing agents, fatty substances, oils, emulsifying and coemulsifying agents, opacifying agents, pearlescent agents, superfatting agents, sequestrants, chelating agents, antioxidants, fragrances, preservatives, conditioning agents, whitening agents intended for the bleaching of the hairs and skin, active principles intended to contribute a treating action with regard to the skin or hair, sunscreens, inorganic fillers or pigments, particles providing a visual effect or intended for the encapsulation of active principles, exfoliating particles, texturizing agents, optical brighteners or insect repellents.

Mention may be made, as examples of thickening and/or gelling polymers optionally present in the composition for which the method which is a subject matter of the present invention is employed, of:
  homopolymers or copolymers of acrylic acid or of acrylic acid derivatives, homopolymers or copolymers of acrylamide, homopolymers or copolymers of acrylamide derivatives, homopolymers or copolymers of acrylamidomethylpropanesulfonic acid, of vinyl monomer and/or of trimethylaminoethyl acrylate chloride sold under the names Carbopol™, Ultrez™ 10, Pemulen™ TR1, Pemulen™ TR2, Simulgel™ EG, Simulgel™ EPG, Luvigel™ EM, Salcare™ SC91, Salcare™ SC92, Salcare™ SC95, Salcare™ SC96, Flocare™ ET100, Flocare™ ET58, Hispagel™, Sepigel™ 305, Sepigel™ 501, Sepigel™ 502, Simulgel™ NS, Simulgel™ 800, Simulgel™ A, Sepiplus™ 250, Sepiplus™ 265, Sepiplus™ 400, Sepinov™ EMT 10, Novemer™ EC1, Aristoflex™ AVC, Aristoflex™ HBM, Rapitix™ A60, Rapitix™ A100, Cosmedia SP and Stabileze™ 06;
  hydrocolloids of vegetable or biosynethetic origin, for example xanthan gum, karaya gum, carrageenates, alginates or galactomannans;
  silicates; cellulose and its derivatives; starch and its hydrophilic derivatives; polyurethanes.

Mention may be made, as examples of thickening and/or gelling surfactants optionally present in the composition for which the method which is a subject matter of the present invention is employed, of:
  fatty esters of alkylpolyglycosides which are optionally alkoxylated and very particularly ethoxylated esters of methylpolyglucoside, such as PEG 120 methyl glucose trioleate and PEG 120 methyl glucose dioleate, respectively sold under the names Glucamate™ LT and Glumate™ DOE120;
  alkoxylated fatty esters, such as PEG 150 pentaerythrityl tetrastearate, sold under the name Crothix™ DS53, or PEG 55 propylene glycol oleate, sold under the name Antil™ 141;
  polyalkylene glycol carbamates comprising fatty chains, such as PPG 14 laureth isophoryl dicarbamate, sold under the name Elfacos™ T211, or PPG 14 palmeth 60 hexyl dicarbamate, sold under the name Elfacos™ GT2125.

Mention may be made, as examples of emulsifiers optionally present in the composition for which the method which is a subject matter of the present invention is employed, of:
  fatty acids, ethoxylated fatty acids, sorbitol fatty acid esters, ethoxylated fatty acid esters, polysorbates, polyglycerol esters, ethoxylated fatty alcohols, sucrose esters, alkylpolyglycosides, sulfated and phosphated fatty alcohols or mixtures of alkylpolyglycosides and of fatty alcohols, such as those described in French patent applications 2 668 080, 2 734 496, 2 756 195, 2 762 317, 2 784 680, 2 784 904, 2 791 565, 2 790 977, 2 807 435, 2 804 432, 2 830 774 and 2 830 445, combinations of emulsifying surfactants chosen from alkylpolyglycosides, combinations of alkylpolyglycosides and of fatty alcohols, and esters of polyglycerols or of polyglycols or of polyols, such as the polyhydroxystearates of polyglycols or of polyglycerols employed in French patent applications 2 852 257, 2 858 554, 2 820 316 and 2 852 258.

Mention may be made, as examples of opacifying and/or pearlescent agents optionally present in the composition for which the method which is a subject matter of the present invention is employed, of sodium or magnesium palmitates or stearates or hydroxystearates, ethylene or polyethylene glycol monostearates or distearates, fatty alcohols, styrene homopolymers and copolymers, such as the styrene/acrylate copolymer sold under the name Montopol™ OP1 by Seppic.

Mention may be made, as examples of oils optionally present in the composition for which the method which is a subject matter of the present invention is employed, of:
  mineral oils, such as liquid paraffin, liquid petrolatum, isoparaffins or white mineral oils;
  oils of animal origin, such as squalene or squalane;
  vegetable oils, such as phytosqualane, sweet almond oil, coconut oil, castor oil, jojoba oil, olive oil, rapeseed oil, peanut oil, sunflower oil, wheatgerm oil, corn oil, soybean oil, cottonseed oil, alfalfa oil, poppy oil, pumpkinseed oil, evening primrose oil, millet oil, barley oil, rye oil, safflower oil, candlenut oil, passion flower oil, hazelnut oil, palm oil, shea butter, apricot kernel oil, *calophyllum* oil, *sisymbrium* oil, avocado oil, *calendula* oil, or oils from flowers or vegetables;
  ethoxylated vegetable oils;
  synthetic oils, such as esters of fatty acids, such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, monoglycerides, diglycerides and triglycerides of fatty acids, such as glycerol triheptanoate, alkyl benzoates, hydrogenated oils, poly(α-olefin)s, polyolefins, such as polyisobutene, synthetic isoalkanes, such as isohexadecane or isododecane, perfluorinated oils, and
  silicone oils, such as dimethylpolysiloxanes, methylphenylpolysiloxanes, silicones modified by amines, silicones modified by fatty acids, silicones modified by alcohols, silicones modified by fatty alcohols and acids, silicones modified by polyether groups, modified epoxy silicones, silicones modified by fluorinated groups, cyclic silicones and silicones modified by alkyl groups.

Mention may be made, as other fatty substance optionally present in the composition for which the method which is a subject matter of the present invention is employed, of fatty alcohols or fatty acids; waxes, such as beeswax, carnauba wax, candelilla wax, ouricury wax, Japan wax, cork fiber wax, sugarcane wax, paraffin waxes, lignite waxes, microcrystalline waxes or lanolin wax; ozokerite; polyethylene wax; silicone waxes; vegetable waxes; fatty alcohols and fatty acids which are solid at ambient temperature; glycerides which are solid at ambient temperature.

Mention may be made, as examples of active principles optionally present in the composition for which the method which is a subject matter of the present invention is employed, of compounds having a lightening or depigmenting action, a moisturizing action, a tightening action, a soothing or relaxing action, an anti-inflammatory action, a slimming action, a lipolytic action, a draining action, a detoxifying action, an energizing action, a decontracting action, a stimulating action, an emollient action, a neuro-modulatory action, a protective action, a purifying action, a seboregulatory action, an anti-hair-loss action, an anti-aging action, a firming, restructuring, free-radical-scavenging or antioxidant action; such active principles are, for example, Sepiwhite™ MSH, arbutin, kojic acid, hydroquinone, ellagic acid, vitamin C and its derivatives, Stay C, magnesium ascorbyl phosphate and its derivatives, ascorbyl glucoside, phytic acid, fruit acids, rucinol or resorcinol, azelaic acid, lipoic acid, Vegewhite™ Gatilune™, Synerlight™, Biowhite™, Phytolight™, Dermalight™, Clariskin™, Melasow™, Dermawhite™, Ethioline, Melarest™, Gigawhite™, Albatine™, Lumiskin™, polyphenol extracts, grape extracts, pine extracts, wine extracts, olive extracts, pond extracts, N-acylated proteins, N-acylated peptides, such as, for example, Matrixil™, N-acylated amino acids, partial hydrolysates of N-acylated proteins, amino acids, peptides, total protein hydrolysates, polyols (for example, glycerol or butylene glycol), milk derivatives, or various components making up the NMF (Natural Moisturizing Factor) composition, for example urea, pyrrolidinecarboxylic acid or derivatives of this acid, amino acids, inorganic salts, glucosamines, glycyrrhetinic acid, α-bisabolol, sugars or sugar derivatives, polysaccharides or derivatives thereof, hydroxy acids, for example lactic acid, vitamins, vitamin derivatives, for example retinol, vitamin E and its derivatives, trace elements, extracts of rocks or stones, enzymes, coenzymes, such as Coenzyme Q10, hormones or "hormone-like" substances, such as, for example, Phyto Age™, soybean extracts, for example Raffermine™, wheat extracts, for example Tensine™ or Gliadine™, plant extracts, such as tannin-rich plant extracts, isoflavone-rich plant extracts or terpene-rich plant extracts, freshwater or saltwater algal extracts, marine extracts in general, such as corals, essential waxes, bacterial extracts, minerals, such as the Givobio™ range, calcium derivatives, magnesium derivatives, copper derivatives, cobalt derivatives, zinc derivatives, lithium derivatives or manganese derivatives, silver salts or gold salts, lipids in general, lipids such as ceramides or phospholipids, active principles having a slimming or lipolytic action, such as caffeine or its derivatives, calcium and its derivatives, Lipaslim™, active principles which improve capillary circulation in the skin, for example veinotonic agents, draining active principles, decongestive active principles such as *ginkgo biloba*, ivy, common horse chestnut, bamboo, *ruscus*, butcher's broom, *centella asiatica*, fucus, rosemary or sage, active principles having an antimicrobial activity or a purifying action on greasy skin, for example Lipacide™ C8G, Lipacide™ UG, Sepicontrol™ A5, copper derivatives or zinc derivatives, Octopirox™ or Sensiva™ SC50, active principles having an energizing or stimulating property, such as Sepitonic™ M3 or Physiogenyl™, panthenol and its derivatives, such as Sepicap™ MP, anti-aging active principles, such as Sepilift™ DPHP, Lipacide™ PVB, Sepivinol™, Sepivital™, Manoliva™, or Phyto-Age™, moisturizing active principles, such as Sepicalm™ S Sepicalm™ VG and Lipacide™ DPHP, active principles for combating photoaging, active principles which protect the integrity of the dermo-epidermal junction, active principles which increase the synthesis of components of the extracellular matrix, for example collagen, elastins, glycosaminoglycans, active principles which act favorably on chemical cell communication, such as cytokines, or physical cell communication, such as integrins, active principles which create a "heating" sensation on the skin, such as skin capillary circulation activators (for example nicotinates) or products which create a sensation of "freshness" on the skin (for example menthol and derivatives).

Mention may be made, as sunscreens optionally present in the composition for which the method which is a subject matter of the present invention is employed, of all those which appear in the amended Cosmetic Directive 76/768/EEC, appendix VII.

The following examples illustrate the invention without, however, limiting it.

A) Preparation of the Compounds of Formula (I) or of Mixtures of Compounds of Formula (I), and of the Concentrates According to the Invention

EXAMPLE 1

Preparation of the concentrate 1 of xylityl glucosides/sodium lauryl ether (2.2 EO) sulfate/xylitol a)—703.0 g of xylitol are introduced into a jacketed glass reactor equipped with an efficient stirrer, a heat-exchange fluid circulating in the jacket.

The xylitol is melted at a temperature of 135° C. and the viscous paste thus obtained is cooled to 115° C.

The glucose is then gradually added to the reaction medium in order to make possible its homogeneous dispersion.

An acid catalytic system composed of 1.29 g of 96% sulfuric acid is added to the mixture thus obtained.

The reaction medium is placed under a partial vacuum of 90 mbar to 45 mbar and maintained at a temperature of 100° C.-105° C. for a time of 4 h 30 with removal of the water formed using a distillation arrangement.

The reaction medium is subsequently cooled to 95° C.-100° C. and neutralized by addition of 5 g of 30% sodium hydroxide in order to bring the pH of a 1% solution of this mixture to a value of 5.0.

The characteristics of the intermediate mixture thus obtained are as follows:
Appearance (visual): orange wax at ambient temperature;
pH 1% solution: 5.0;
Residual xylitol: 55.8%;
Residual glucose: <1%;
Xylityl glucosides: 37.2% b)—15.86 g of the intermediate mixture obtained above and 383.15 g of 28% sodium lauryl ether (2.2 EO) sulfate in water are mixed at 50° C. in a jacketed glass reactor equipped with an efficient stirrer, a heat-exchange fluid circulating in the jacket. After obtaining a homogeneous mixture, the composition by weight of the concentrate 1 obtained is as follows for a solids content of 100%:
Sodium lauryl ether (2.2 EO) sulfate=70%
Xylityl glucosides=12%
Xylitol=18%

Starting from the same intermediate mixture obtained in section a) and using appropriate proportions by weight of 28% sodium lauryl ether (2.2 EO) sulfate in water, the concentrates 1a and 1b are obtained so as to respectively comprise 60% by weight and 50% by weight on a dry basis of sodium lauryl ether (2.2 EO) sulfate. The compositions by weight of these concentrates are described in table 1 below.

EXAMPLE 2

Preparation of the Concentrate 2 of Diglyceryl Glucosides/Sodium Lauryl Ether (2.2 EO) Sulfate/Digylcerol a)—645.0 g of diglycerol are introduced into a jacketed glass reactor equipped with an efficient stirrer, a heat-exchange fluid circulating in the jacket. The diglycerol is brought to a temperature of approximately 100° C.

139.9 g of glucose are then gradually added to the reaction medium in order to make possible its homogeneous dispersion.

An acid catalytic system composed of 0.97 g of 98% sulfuric acid is added to the mixture thus obtained.

The reaction medium is placed under a partial vacuum of 30 mbar and maintained at a temperature of 100° C.-105° C. for a time of 4 h 00 with removal of the water formed using a distillation arrangement.

The reaction medium is subsequently cooled to 95° C.-100° C. and neutralized by addition of 30% sodium hydroxide in order to bring the pH of a 1% solution of this mixture to a value of approximately 7.0.

The characteristics of the intermediate mixture thus obtained are as follows:
Appearance (visual): clear liquid;
pH 1% solution: 6.8;
Residual diglycerol: 67.2%;
Residual glucose: <1%;
Diglyceryl glucosides: 24.7% b)—20.0 g of the intermediate mixture obtained above and 166.7 g of 28% sodium lauryl ether (2.2 EO) sulfate in water are mixed at 50° C. in a jacketed glass reactor equipped with an efficient stirrer, a heat-exchange fluid circulating in the jacket. After obtaining a homogeneous mixture, the composition by weight of the concentrate 2 obtained is as follows for a solids content of 100%:
Sodium lauryl ether (2.2 EO) sulfate=70%
Diglyceryl glucosides=8%
Diglycerol=22%

Starting from the same intermediate mixture obtained in stage a) and using suitable proportions by weight of 28% sodium lauryl ether (2.2 EO) sulfate in water, the concentrates 2a and 2b are obtained so as to respectively comprise 60% by weight and 50% by weight on a dry basis of sodium lauryl ether (2.2 EO) sulfate. The compositions by weight of these concentrates are described in table 1 below.

COMPARATIVE EXAMPLES 2 AND 3

Comparative examples 2 and 3 are prepared according to the following method:
introduction of 28% sodium, lauryl ether (2.2 EO) sulfate in water into a beaker at ambient temperature.
The medium is stirred with a magnetic bar coupled to a magnetic stirrer and the polyol (xylitol for comparative example 2 and diglycerol for comparative example 3) is gradually introduced in proportions which make it possible to achieve a concentrate comprising 50% by weight on a dry basis of sodium lauryl ether (2.2 EO) sulfate and 50% by weight of polyol.

COMPARATIVE EXAMPLE 4

Comparative example 4 is prepared according to the following method:
introduction of 28% sodium lauryl ether (2.2 EO) sulfate in water into a beaker at ambient temperature.
The medium is stirred with a magnetic bar coupled to a magnetic stirrer and PEG-40 glyceryl cocoate is gradually introduced in proportions which make it possible to achieve a concentrate comprising 70% by weight on a dry basis of sodium lauryl ether (2.2 EO) sulfate and 30% by weight of PEG-40 glyceryl cocoate.

COMPARATIVE EXAMPLE 5

Comparative example 5 is prepared according to the following method:
introduction of 28% sodium lauryl ether (2.2 EO) sulfate in water into a beaker at ambient temperature.
The medium is stirred with a magnetic bar coupled to a magnetic stirrer and PEG-80 sorbitan laurate is gradually introduced in proportions which make it possible to achieve a concentrate comprising 70% by weight on a dry basis of sodium lauryl ether (2.4 EO) sulfate and 30% by weight of PEG-80 sorbitan laurate.
Summarizing Table The compositions by weight on a dry basis of the various concentrates prepared above and intended to be employed in a test for evaluating the ocular tolerance are summarized in table 1 below.

TABLE 1 compositions by weight on a dry basis of the concentrates prepared for the evaluation of ocular tolerance.

|  | Sodium lauryl ether (2.2 EO) sulfate | Xylityl glucosides | Diglyceryl glucosides | Xylitol | Diglycerol | PEG-40 glyceryl cocoate | PEG-80 sorbitan laurate |
|---|---|---|---|---|---|---|---|
| Concentrate 1 | 70% | 12% | — | 18% | — | — | — |
| Concentrate 1a | 60% | 16% | — | 24% | — | — | — |
| Concentrate 1b | 50% | 20% | — | 30% | — | — | — |
| Concentrate 2 | 70% | — | 8% | — | 22% | — | — |
| Concentrate 2a | 60% | — | 11% | — | 29% | — | — |
| Concentrate 2b | 50% | — | 14% | — | 36% | — | — |
| Comparative example 1 | 100% | — | — | — | — | — | — |
| Comparative example 2 | 50% | — | — | 50% | — | — | — |
| Comparative example 3 | 50% | — | — | — | 50% | — | — |

TABLE 1-continued compositions by weight on a dry basis of the concentrates prepared for the evaluation of ocular tolerance.

|  | Sodium lauryl ether (2.2 EO) sulfate | Xylityl glucosides | Diglyceryl glucosides | Xylitol | Diglycerol | PEG-40 glyceryl cocoate | PEG-80 sorbitan laurate |
|---|---|---|---|---|---|---|---|
| Comparative example 4 | 70% | — | — | — | — | 30% | — |
| Comparative example 5 | 70% | — | — | — | — | — | 30% |

B)—Demonstration of the Properties of the Compounds of Formula (I) or of Mixtures of Compounds of Formula (I), and of Concentrates According to the Invention 1—Choice of the Evaluation Method The properties of the compounds of formula (I) or of the mixtures of compounds of formula (I) and of the concentrates defined above forming the subject matter of the invention can be demonstrated by the use of several in vitro evaluation methods; the latter being preferred to in vivo methods for ethical reasons and for their ease of implementation.

The in vitro methods include the RBCA test, which measures the effects of the products on the cytoplasmic membrane by the determination of the half-hemolysis concentration, the interpretation of which by the Pape classification is carried out by the hemolysis/denaturation ratio (1992, INVITTOX data bank, protocol No. 37, Russel & Burch, 96-98 North Sherwood, Nottingham, UK), and the HET-CAM method (see references below).

These in vitro methods can be regarded as alternatives to the Draize test, as described by the OECD 405 protocol, carried out on the animal (rabbit).

The results of the HET-CAM test exhibit an excellent correlation with the results of the Draize test on the alkylpolyglycoside family; however, as the membrane of the egg is much more sensitive than the cornea of the eye, a factor of 10 makes it possible to obtain perfect correspondence: the same result is obtained for a test dose 10 times smaller in the HET-CAM test. The in vitro method selected to demonstrate the qualities of ocular nonirritation in the context of the present invention is thus the HET-CAM method.

2—Principle of the HET-CAM Method Selected

The properties of ocular nonirritation of the compounds of formula (I) or of the mixtures of compounds of formula (I) and of the concentrates defined above relating to the invention were demonstrated by a test on the hen's egg chorioallantoic membrane, known as the "HET-CAM" (Hen's Egg Test ChorioAllantoic Membrane) test".

The experimental protocol of this test is adapted from the Luepke publication (The Hen's Egg Test: "An Alternative Toxicity Test", Brit. J. Dermato., 1986, 115. Suppl. 31, 133-135, Luepke N. P. & Kemper F. H. The HET-CAM Test: "An Alternative to the Draize Test", Food Chem. Toxicol., 1986, 24, No. 6/7, 495-496), from the INVITTOX No. 47 protocol (1992, INVITTOX data bank, 34 Stoney Street, Nottingham, NG1 1NB, UK) and from Annex IV to the order published in the Official Journal of the French Republic of 26 Dec. 1996 relating to the official methods for the analysis of beauty products (NOR: FCEC9600217A).

This tests consists in assessing the irritation potential of a substance by reading the modifications observed after application of a solution of this substance to the richly vascularized chorioallantoic membrane of the preincubated Leghorn hen's egg.

3—Experimental Protocol

The products were tested at an active material concentration of 1%. The solutions are prepared by diluting in deionized water at most 24 hours in advance.

The pH of the test solutions is adjusted to 7 with triethanolamine or lactic acid, if necessary.

On reception, the fertilized eggs are preincubated in an incubator for 10 days at 37.8° C.±0.5° C. with a degree of humidity in the incubator of 50% to 60%.

The shell of the eggs on which the tests are carried out is cut out around the air pocket and the chorioallantoic membrane is uncovered by carefully removing the shell membrane using tweezers.

0.3 cm$^3$ of the solution to be tested is deposited at the surface of the membrane.

20 seconds later, the membrane is rinsed with 5 cm$^3$ of deionized water at 37° C. for 10 seconds.

The following are noted over a time interval of 5 minutes: the beginning of hyperemia (time $t_1$), the beginning of bleeding (time $t_2$), and the beginning of clotting (time $t_3$).

By definition, if one of the phenomena has not appeared during these five minutes (300 seconds), it is recorded $t_i$=301 seconds.

4—Expression of the Results

Each solution is tested on 4 to 6 eggs according to the repeatability of the reactions observed. The Het-Cam index I, representative of the test, is calculated for each egg tested in the following way:

$$I = 5 \times (301-t_1)/300 + 7 \times (301-t_2)/300 + 9 \times (301-t_3)/300$$

The mean of the individual indices is subsequently calculated, along with the statistical uncertainty i:

$$i = t \cdot S/\sqrt{n} \text{ for a risk of 5\%}$$

The following scale of the index I is adopted for the interpretation of the results:

| Het-Cam index | Classification of the compound tested |
|---|---|
| I < 1 | Nonirritating |
| 1 ≦ I < 5 | Slightly irritating |
| 5 ≦ ... I < 9 | Moderately irritating |
| 9 ≦ ... I < 12 | Irritating |
| I ≧ 12 | Severely irritating |

In view of the correspondence factor between this test, in vitro, and in vivo, the result obtained by the HET-CAM test for a 1% AM solution is equivalent to that obtained for a 10% AM in vivo.

5—Influence of the Compounds of Formula (I) or of the Mixtures of Compounds of Formula (I) on the Ocular Tolerance of Compounds of Formula (II)

5.1. Results Obtained

TABLE 2

Results of the Het-Cam tests on the concentrates prepared.

|  | Het-Cam index | Classification of the concentrate tested |
|---|---|---|
| Concentrate 1 | 3.0 | Slightly irritating |
| Concentrate 1a | 0.9 | Nonirritating |
| Concentrate 1b | 0 | Nonirritating |
| Concentrate 2 | 3.0 | Slightly irritating |
| Concentrate 2a | 2.4 | Slightly irritating |
| Concentrate 2b | 0.9 | Nonirritating |
| Comparative example 1 | 10.7 | Irritating |
| Comparative example 2 | 8.2 | Moderately irritating |
| Comparative example 3 | 9.0 | Irritating |
| Comparative example 4 | 6.0 | Moderately irritating |
| Comparative example 5 | 10.5 | Irritating |

5.2. Analysis of the Results

The results are judged to be satisfactory and consequently the method according to the invention is effective if the concentrate tested shows an HET-CAM index of less than 5 and preferably less than or equal to 3.

The foaming surfactants of formula (II) are classified as "irritating" according to the HET-CAM test in force (comparative example 1).

The combination with ethoxylated nonionic surfactants at a level of 30% by weight, known by a person skilled in the art to make it possible to reduce ocular irritation (comparative example 4 and comparative example 5), does not make it possible to achieve the minimum "slightly irritating" classification necessary for use in a cosmetic, dermocosmetic, dermopharmaceutical or pharmaceutical composition for cutaneous application which may be in contact with the eyes of the user.

The combination of the surfactants of formula (II) with polyols which can constitute a topically acceptable solvent according to the invention does not make it possible to achieve the minimum "slightly irritating" classification necessary for use in a cosmetic, dermocosmetic, dermopharmaceutical or pharmaceutical composition for cutaneous application which may be in contact with the eyes of the user (comparative example 2 and comparative example 3).

It is necessary to combine 12% by weight of compounds of formula (I) or of mixture of compounds of formula (I) having a xylityl chain with sodium lauryl ether (2.2 EO) sulfate of comparative example 1 (concentrate 1 according to the invention) to bring the concentrate comprising the surfactants of formula (II) to the "slightly irritating" classification and 16% by weight of compounds of formula (I) or of a mixture of compounds of formula (I) having a xylityl chain with sodium lauryl ether (2.2 EO) sulfate of comparative example 1 (concentrate 1a according to the invention) to bring the concentrate to the "nonirritating" classification.

It is necessary to combine 8% by weight of compounds of formula (I) or of mixture of compounds of formula (I) having a diglyceryl chain with sodium lauryl ether (2.2 EO) sulfate of comparative example 1 (concentrate 2 according to the invention) to bring the concentrate comprising the surfactants of formula (II) to the "slightly irritating" classification and 14% by weight of compounds of formula (I) or of a mixture of compounds of formula (I) having a diglyceryl chain with sodium lauryl ether (2.2 EO) sulfate of comparative example 1 (concentrate 2b according to the invention) to bring the concentrate to the "nonirritating" classification.

C)—Formulations

In the following formulations, the percentages are expressed by weight of the formulation.

C.1 Face Makeup-Removing Fluid

| Formulation | |
|---|---|
| Concentrate 1 | 10.00% |
| Methylparaben | 0.15% |
| Phenoxyethanol | 0.80% |
| Sepicalm ™ S | 1.00% |
| Fragrance/Scent | 0.10% |
| Water | q.s. 100.00% |

Procedure: the various ingredients are mixed in water with magnetic stirring in the order shown and the pH is adjusted to the vicinity of 7.

C.2 Hair and Body Shampoo for Children

| | Formulation | |
|---|---|---|
| A | Concentrate 2 | 15.00% |
| | Proteol ™ APL | 5.00% |
| | Sepicide ™ HB | 0.50% |
| | Fragrance/Scent | 0.10% |
| B | Water | 20.00% |
| | Capigel ™ 98 | 3.50% |
| C | Water | q.s. 100.00% |
| | Sepicide ™ CI | 0.30% |
| | Colorant | q.s. |
| | Sodium hydroxide | q.s. pH = 7.2 |

Procedure: the concentrate 2 is mixed with the Proteol™ APL and the Sepicide™ HB (phase A). The Capigel™ 98 is diluted in a portion of the water and added to the phase A obtained above (phase B). The remaining water is added to the phase B, followed by the Sepicide™ CI and the colorant. The pH of the mixture is adjusted to approximately 7.2 with sodium hydroxide.

C.3 Makeup-Removing Wipes for the Eyes

| | Formulation | |
|---|---|---|
| A | Concentrate 1 | 3.00% |
| B | Seipicide ™ HB2 | 0.50% |
| C | Sepicalm ™ VG | 0.50% |
| | Glycerol | 10.00% |
| | Fragrance/Scent | 0.05% |
| D | Water | q.s. 100.00% |

Procedure: the ingredients of the phase B and also of the phase C are mixed in the phase A until the solution is clear. The phase D is added.

C.4 Mild Foaming Gel

| | Formulation | |
|---|---|---|
| A | Concentrate 2 | 8.50% |
| | Proteol™ APL | 3.00% |
| | Euxyl™ PE9010 | 1.00% |
| | Fragrance/Scent | 0.10% |
| B | Water | q.s. 100.00% |
| | Lactic acid | q.s. pH = 6.0 |

Procedure: the fragrance and the preservative Euxyl™ PE9010 are dissolved in the mixture composed of the concentrate 2 and of Proteol™ APL (phase A). The water is added and the pH is adjusted to approximately 6.0 with lactic acid.

C.5 Shampoo for Frequent Use

| | Formulation | |
|---|---|---|
| A | Concentrate 2 | 12.80% |
| | Proteol™ OAT | 5.00% |
| | Euxyl™ PE9010 | 1.00% |
| | Fragrance/Scent | 0.30% |
| | Water | q.s. 100.00% |
| B | Montaline™ C40 | 8.50% |
| | Lactic acid | q.s. pH = 6.0 |

Procedure: all the ingredients of the phase A are mixed and, after homogenization, the Montaline™ C40 is added and the pH is adjusted to approximately 6.0 using lactic acid.

C.6 Ultramild Shampoo for Babies

| | Formulation | |
|---|---|---|
| A | Concentrate 2 | 10.00% |
| | Amisoft™ CS-11 | 4.00% |
| | Fragrance/Scent | 0.10% |
| | Sepicide™ HB | 0.30% |
| | Sepicide™ CI | 0.20% |
| | Water | q.s. 100.00% |
| B | Water | 20.00% |
| | Capigel™ 98 | 3.50% |
| | Tromethamine | q.s. pH = 7.2 |

Procedure: all the ingredients of the phase A are mixed in the order shown until a clear phase A is obtained. The Capigel™ 98 is separately added to the water, then this phase B, thus prepared, is added to the phase A and the pH is adjusted to 7.2 using tromethamethamine.

C.7 Cleansing Milk for Babies

| | Formulation | |
|---|---|---|
| A | Simulsol™ 165 | 2.00% |
| | Montanov™ 202 | 1.00% |
| | Lanol™ 99 | 3.00% |
| | Dimethicone | 1.00% |
| | Isohexadecane | 3.00% |
| B | Water | q.s. 100.00% |
| C | Sepiplus™ 400 | 0.30% |
| D | Concentrate 2 | 6.35% |
| E | Sepicide™ HB | 0.30% |
| | DMDM Hydantoin | 0.20% |
| | Fragrance/Scent | 0.10% |

Procedure: the phases A and B, formed by mixing the various constituents, are heated separately: the phase C is added to the hot fatty phase and the emulsion is produced by running in the aqueous phase; the mixture is homogenized for a few minutes with vigorous stirring (via a rotor/stator turbine). The phase D is then added to the hot emulsion, which is cooled with moderate stirring until it has returned to ambient temperature. The phase E is added at 40° C.

C.8 Cleansing Powder Lotion for Sensitive Skin

| | Formulation | |
|---|---|---|
| A | Lipacid™ C8G | 0.95% |
| | Methylparaben | 0.10% |
| | Ethylparaben | 0.024% |
| | Propylparaben | 0.0119% |
| | Butylparaben | 0.024% |
| | Isobutylparaben | 0.0119% |
| | Water | 20.00% |
| | Disodium EDTA | 0.10% |
| | Triethanolamine | 1.38% |
| B | Concentrate 2 | 1.80% |
| | Fragrance/Scent | 0.10% |
| C | Sepicalm™ S | 0.28% |
| | Water | q.s. 100.00% |
| | Lactic acid | q.s. pH = 5.2 |
| D | Micropearl™ M310 | 5.00% |

Procedure: the ingredients of the phase A are dissolved in water at 80° C. The fragrance is dissolved separately in the concentrate 2 to prepare the phase B. The cooled phase A is added to the phase B and then the Sepicalm™ S and the remaining water are introduced. The final pH is checked and optionally adjusted to approximately 5.2. The Micropearl™ M310 is then added.

The characteristics of the products used in the preceding examples are as follows:

Sepicalm™ S is a mixture of N-cocoylamino acids, of sarcosine, of potassium aspartate and of magnesium aspartate as described in WO 98/09611, sold by Seppic.

Proteol™ APL is a mixture of N-cocoylamino acids in the form of sodium salts which are obtained by acylation of the characteristic amino acids of apple juice, sold by Seppic.

Sepicide™ HB, a mixture of phenoxyethanol, of methylparaben, of ethylparaben, of propylparaben and of butylparaben, is a preservative sold by Seppic.

Capigel™ 98 is a copolymer of acrylates, sold by Seppic.

Sepicide™ CI, imidazoline urea, is a preservative, sold by Seppic.

Sepicide™ HB2, a mixture of phenoxyethanol, methylparaben, ethylparaben, propylparaben, butylparaben and isobutylparaben, is a preservative, sold by Seppic.

Sepicalm™ VG is a mixture of N-palmitoylproline in the sodium salt form and of extracts of flowers of *Nymphaea alba*, sold by Seppic.

Euxyl™ PE9010, a mixture of phenoxyethanol and of ethylhexylglycerin, is a preservative sold by Seppic.

Proteol™ OAT is a mixture of N-lauroylamino acids obtained by complete hydrolysis of oat protein, as described in WO 94/26694, sold by Seppic.

Montaline™ C40 is a monoethanolamine cocamidopropyl betainamide chloride salt.

Amisoft™ CS-11 is a disodium salt of N-cocoylglutamate, sold by Ajinomoto.

Simulsol™ 165 is a mixture of PEG-100 stearate and of glyceryl stearate, sold by Seppic.

Montanov™ 202 (arachidyl alcohol, behenyl alcohol and arachidyl glucoside) is a self-emulsifiable composition, such as those described in EP 0 977 626, sold by Seppic.

Lanol™ 99 is isononyl isononanoate, sold by Seppic.

Sepiplus™ 400 is a self-invertible inverse latex of polyacrylates in polyisobutene which comprises polysorbate 20, as described in WO 2005/040230, sold by Seppic.

Lipacid™ C8G is capryloyl glycine, sold by Seppic.

Micropearl™ M310 is a crosslinked polymethyl methacrylate polymer which is provided in a powder form and which is used as texture modifier.

What is claimed is:

1. A concentrate, consisting of, per 100% by weight:
   from 8% to 90% by weight of a compound of formula (I):

$$R_1-O-(G)_x-H \quad (I)$$

in which:
   x represents a decimal number of between 1 and 5,
   G represents the residue of glucose, and
   $R_1$ represents a monovalent radical of formula (A):

$$-CH_2-(CHOH)_n-CH_2-OH \quad (A)$$

in which n is 3;
   from 2% to 99% by weight of a compound of formula (II):

$$[R_2-O-(CH_2-CH_2-O)_p-SO_3]_rX \quad (II)$$

in which:
   $R_2$ represents a saturated or unsaturated and linear or branched aliphatic hydrocarbon radical comprising from 6 to 22 carbon atoms,
   p represents a decimal number of between 1 and 10, preferably between 2 and 4,
   r is an integer equal to 1 or to 2, and
   X represents the cation of an alkali metal or an alkaline earth metal, ammonium ion, (hydroxyethyl)ammonium ion or tri(hydroxyethyl)ammonium ion,
   or of a mixture of compounds of formula (II); and
   from 0% to 80% by weight of a topically acceptable solvent.

2. The concentrate as defined in claim 1, wherein, in the formula (II), $R_2$ represents a saturated aliphatic hydrocarbon radical comprising from 8 to 18 carbon atoms.

3. The concentrate as defined in claim 1, consisting of, per 100% by weight:
   from 8% to 50% by weight of a compound of formula (I),
   from 10% to 95% by weight of a compound of formula (II) or of a mixture of compounds of formula (II), and
   from 0 to 80% by weight of a topically acceptable solvent.

4. The concentrate as defined in claim 1, wherein the topically acceptable solvent comprises one or more components selected from the group consisting of water, glycols, polyols, alcohols, alkoxylated polyols and glycol ethers.

5. A process for the preparation of a concentrate as defined in claim 1, the process comprising:
   a stage (a) of mixing, with stirring, a compound of formula (I) with a compound of formula (II) or a mixture of compounds of formula (II) and, if necessary,
   a stage (b) of mixing, with stirring, the combination prepared in stage (a) with a topically acceptable solvent.

6. The concentrate as defined in claim 2, consisting of, per 100% by weight:
   from 8% to 50% by weight of a compound of formula (I),
   from 10% to 95% by weight of a compound of formula (II) or of a mixture of compounds of formula (II), and
   from 0 to 80% by weight of a topically acceptable solvent.

7. The concentrate as defined in claim 2, wherein the topically acceptable solvent comprises one or more components selected from the group consisting of water, glycols, polyols, alcohols, alkoxylated polyols and glycol ethers.

* * * * *